United States Patent
May et al.

(10) Patent No.: US 8,088,128 B2
(45) Date of Patent: Jan. 3, 2012

(54) IMPLANTABLE CROSS-PIN FOR ANTERIOR CRUCIATE LIGAMENT REPAIR

(75) Inventors: Thomas C. May, Wrentham, MA (US); Greg Whittaker, Stoneham, MA (US)

(73) Assignee: DePuy Mitek, Inc., Raynham, MA (US)

( * ) Notice: Subject to any disclaimer, the term of this patent is extended or adjusted under 35 U.S.C. 154(b) by 195 days.

(21) Appl. No.: 10/808,764

(22) Filed: Mar. 25, 2004

(65) Prior Publication Data
US 2005/0216014 A1    Sep. 29, 2005

(51) Int. Cl.
- A61B 17/56    (2006.01)
- A61B 17/58    (2006.01)
- A61F 2/30    (2006.01)
- A61F 2/08    (2006.01)

(52) U.S. Cl. ............... 606/64; 623/13.12; 623/13.14
(58) Field of Classification Search .............. 606/64, 606/72, 73, 96; 623/13.11, 13.14, 13.12
See application file for complete search history.

(56) References Cited

U.S. PATENT DOCUMENTS

| | | | |
|---|---|---|---|
| 4,968,315 A * | 11/1990 | Gatturna | 606/139 |
| 5,102,421 A * | 4/1992 | Anspach, Jr. | 606/232 |
| 5,211,647 A * | 5/1993 | Schmieding | 606/104 |
| 5,257,996 A | 11/1993 | McGuire | |
| 5,269,809 A * | 12/1993 | Hayhurst et al. | 606/232 |
| 5,474,554 A * | 12/1995 | Ku | 606/74 |
| 5,480,403 A * | 1/1996 | Lee et al. | 606/72 |
| 5,702,397 A * | 12/1997 | Goble et al. | 606/232 |
| 5,733,307 A * | 3/1998 | Dinsdale | 606/232 |
| 5,849,013 A | 12/1998 | Whittaker et al. | |
| 5,885,294 A * | 3/1999 | Pedlick et al. | 606/80 |
| 5,993,459 A * | 11/1999 | Larsen et al. | 606/104 |
| 6,113,604 A | 9/2000 | Whittaker et al. | |
| 6,132,433 A | 10/2000 | Whelan et al. | |
| 6,306,138 B1 | 10/2001 | Clark et al. | |
| 6,508,830 B2 * | 1/2003 | Steiner | 606/232 |
| 6,540,783 B1 | 4/2003 | Whittaker et al. | |
| 6,579,295 B1 * | 6/2003 | Supinski | 606/72 |
| 6,623,524 B2 | 9/2003 | Schmieding | |
| 7,338,492 B2 * | 3/2008 | Singhatat et al. | 606/232 |
| 2002/0019635 A1 | 2/2002 | Wenstrom, Jr. et al. | |
| 2002/0058941 A1 | 5/2002 | Clark et al. | |
| 2002/0087160 A1 | 7/2002 | Clark et al. | |
| 2002/0133165 A1 | 9/2002 | Whittaker et al. | |
| 2002/0156484 A1 | 10/2002 | McKernan et al. | |
| 2003/0009217 A1 | 1/2003 | McKernan et al. | |
| 2003/0130666 A1 | 7/2003 | Whittaker et al. | |
| 2004/0133239 A1 * | 7/2004 | Singhatat | 606/232 |
| 2005/0033301 A1 | 2/2005 | Lombardo et al. | |
| 2005/0159812 A1 * | 7/2005 | Dinger et al. | 623/13.14 |

FOREIGN PATENT DOCUMENTS

EP        0 829 233 A    3/1998

OTHER PUBLICATIONS

EP Search Report dated Jan. 27, 2008 for EP Application No. 05251849.5.

* cited by examiner

Primary Examiner — Thomas Barrett
Assistant Examiner — David Bates

(57) ABSTRACT

A novel cross-pin for use in ACL reconstructive surgical procedures. The cross-pin has an elongated body having a distal tapered end. A guide wire opening in the distal end is in communication with a tunnel contained in the distal end. There is a trough extending into the outer surface of the trough for receiving a guide wire. The trough is in communication with the tunnel.

5 Claims, 6 Drawing Sheets

IMPLANTABLE CROSS-PIN FOR ANTERIOR CRUCIATE LIGAMENT REPAIR

TECHNICAL FIELD

The technical field to which this invention relates is orthopedic implants, in particular, orthopedic implants useful for anterior cruciate ligament repair procedures.

BACKGROUND OF THE INVENTION

The anterior cruciate ligament (ACL) is a major component of the soft tissue in a human knee that is responsible for stability of the knee. In addition to the ACL, several other ligaments provide stability including the posterior cruciate ligament (PCL) and the medial and lateral collateral ligaments (MCL/LCL). It is not uncommon for a person to rupture or tear the ACL during various types of physical activities including sports, work, and the like. The tear or rupture can be caused by trauma such as impact, or by abrupt stopping or turning movements which cause exceptional forces to be transmitted to the ACL. Typically a torn or ruptured ACL cannot be repaired using conventional soft tissue repair procedures such as suturing, stapling, etc. It is necessary to replace the ACL with a graft. The graft may be an autograph harvested, for example, from the patient's patellar tendon or hamstring tendon, an allograft harvested from a cadaver, a xenograft, or an artificial man-made tendon. Tissue-engineered ligaments may also be available. In a typical ACL reconstruction, axial tunnels are drilled into the patient's tibia and femur by the surgeon using conventional surgical drills, drill guides and instruments. Once the knee is prepared, the graft is then inserted by the surgeon into the tibial and femoral tunnels, such that one end of the graft resides in each tunnel. The graft is adjusted by the surgeon to provide the desired range of motion. Finally, the graft is secured at both ends in a conventional manner to complete the ACL repair or reconstruction. For example, the graft ends may be secured with conventional interference screws, etc. An alternate method of securement is to use a cross-pin, in particular a femoral cross-pin. In this type of procedure, a transverse hole is drilled into the end of femur such that it intersects the femoral tunnel, and a guide wire is threaded through the transverse tunnel. A cannulated cross-pin is then inserted into the transverse tunnel over the guide wire and underneath a looped end of the graft in order to secure the graft in the femoral tunnel. The guide wire is then removed. If desired, the other end of the graft may be secured in the tibial tunnel by a tibial cross-pin in a similar manner.

Although the cannulated cross-pins known in this art are sufficient and adequate for their intended purposes, there is a continuing need in this art for improved cross-pins and surgical techniques. For example, there is a need for novel cross-pins that provide uni-cortical fixation and intraoperative removal or revision, eliminate or reduce the need for multiple size (length) implants, and simplify the need to make measurements and calculations in order to determine appropriate length.

Accordingly, there is a need in this art for novel cannulated cross-pins for use in ACL reconstruction procedures.

SUMMARY OF THE INVENTION

A novel cross-pin for use in ACL reconstruction procedures is disclosed. The cross-pin has an elongated member having a proximal end, a distal end, an outer surface, and a longitudinal axis. A nose member extends out from the distal end. The nose member has a proximal end and a distal end. There is an axial trough in the member extending through the outer surface. The trough has a proximal end, a distal end, a bottom, an open top and a passageway. There is a guide-wire opening in the distal end of the nose member. There is also an interior passage in the nose member that extends from the guide-wire opening through to the trough such that the passage is in communication with the guide wire opening and the trough.

Another aspect of the present invention is a method of securing the end of an ACL ligament implant in a bone tunnel using the above-described implantable cross-pin.

These and other aspects and characteristics of the present invention will become more apparent from the following description and accompanying drawings.

DETAILED DESCRIPTION OF THE INVENTION

The cross-pins of the present invention can be made from a variety of conventional biocompatible materials useful in implants. The materials may be absorbable or non-absorbable. Examples of conventional non-absorbable materials include surgical stainless steel, nickel titanium alloys, ceramics, Delrin, polyethylene, and other non-absorbable polymers including, but not limited to, polypropylene, and Acetal. Examples of bioabsorbable materials include PLA, PGA, polydioxanone, polycaprolactone, copolymers thereof, and the like. The term "natural polymer" refers to polymers that are naturally occurring, as opposed to synthetic polymers. In embodiments where the device includes at least one synthetic polymer, suitable biocompatible synthetic polymers can include polymers selected from the group consisting of aliphatic polyesters, poly(amino acids), copoly(etheresters), polyalkylenes oxalaes, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethane) and blends thereof. Suitable synthetic polymers for use in the present invention can also include biosynthetic polymers based on sequences found in collagen, elastin, thrombin, fibronectin, starches, poly(amino acid), poly(propylene fumarate), geletin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combination thereof. The devices of the present invention may also be manufactured from conventional biocompatible natural polymers. If desired, the bioabsorbable materials may contain osteoinductive or osteoconductive materials, polymers and blends of polymers including but not limited to calcium hydroxyapatite, tricalcium phosphate, and the like.

The cross-pins of the present invention may be made using a variety of conventional manufacturing processes including machining, molding, etc., and combinations thereof.

Figure 1:
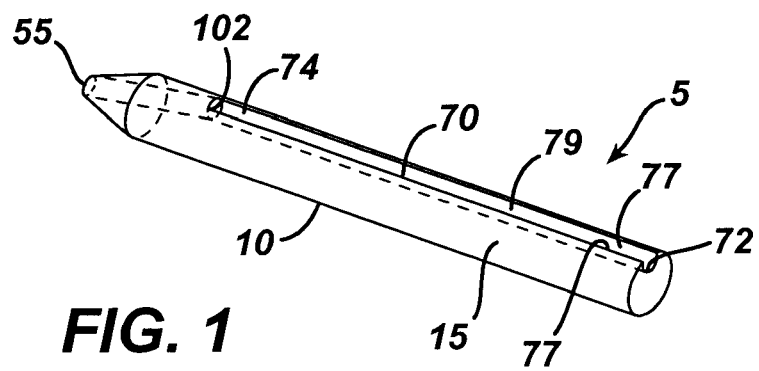
FIG. 1 is a perspective view of the cross-pin of the present invention.
Figure 2:
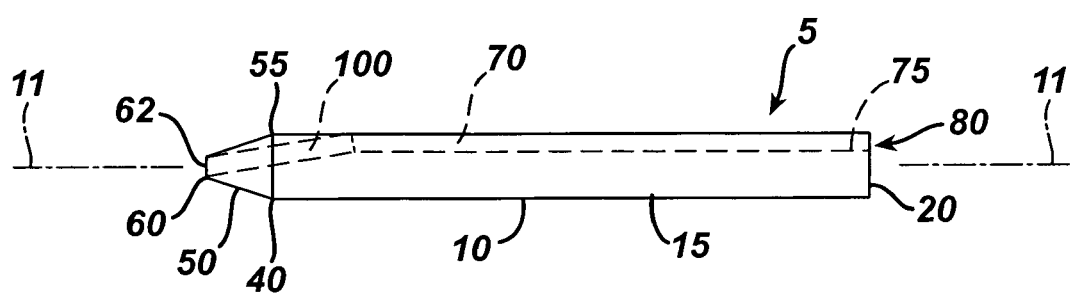
FIG. 2 is a top view of the cross-pin of FIG. 1.

As seen in FIG. 1, a cross-pin 5 of the present invention has an elongated member 10. The member 10 has proximal end 20 and distal end 40. The member 10 is seen to have a longitudinal axis 11. Extending from the distal end 40 is the nose member 50 having proximal end 55 and distal end 60. Member 50 may have a variety of geometric configurations including tapered, conical, frustoconical, bullet-shaped, rounded, stepped, etc., and combinations thereof. Extending into the outer surface 15 of the member 10 is the axial trough 70. Trough 70 is seen to have open proximal end 72, distal end 74, bottom 75, opposed sides 77. Trough 70 may have a variety of cross-sections, including U-shaped, circular, arcuate, square, rectangular, etc. and combinations thereof. Trough 70 is also seen to have open top 79 extending through surface 15. The trough 70 also has passage 80. The nose member 50 is seen to have a guide wire opening 62 at its distal end 55, which is preferably located concentrically about the longitudinal axis 11. Nose end member 50 is seen to contain a tunnel 100 extending through to trough 70. Tunnel 100 is seen to have passage 102 that is in communication with the guide wire opening 62 in the nose end member 50 and also in communication with the trough passage 80 at distal end 74.

The cross-pin of the present is used in combination with a conventional guide wire in order to secure an ACL replacement ligament graft into a femoral tunnel. A variety of methods of securing ACL replacement ligament grafts in femoral tunnels using conventional cannulated cross-pins are known in the art. For example U.S. patent application Ser. No. 10/439,752, which is incorporated by reference, discloses a method of moving an ACL graft into a femoral tunnel and securing it with a cannulated cross-pin moved over a guide wire.

Figure 3:
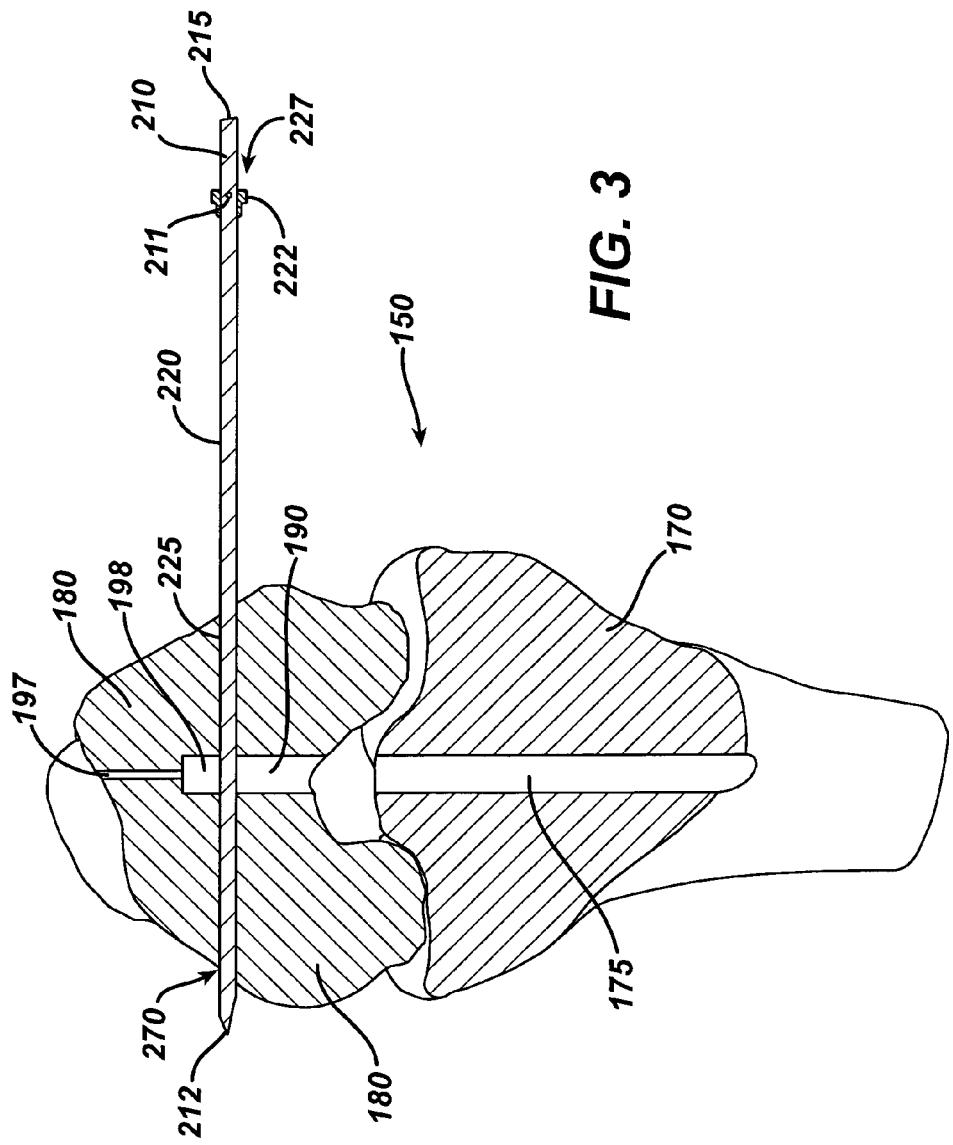
FIG. 3 is a partial cross-section of a knee illustrating a cross-section of the bottom of a femur in the knee having a femoral tunnel with a transverse tunnel; a cannula sleeve is illustrated in the transverse tunnel along with a trocar/drill used to drill the transverse tunnel and emplace the cannula sleeve. Also illustrated is a cross-section of the top of a tibia in the knee having a tibial tunnel.
Figure 4:
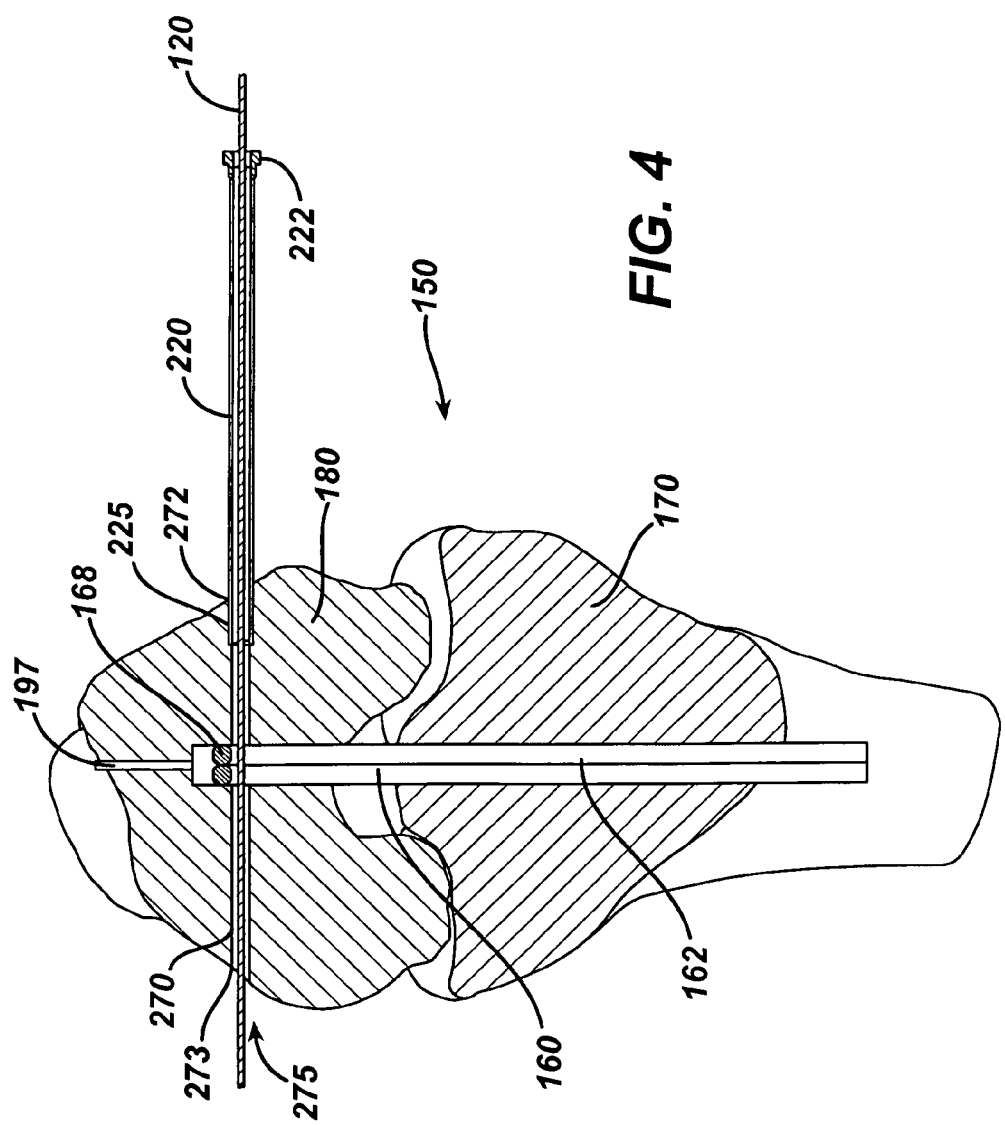
FIG. 4 illustrates the femur of the knee of FIG. 3 after the transverse tunnel has been drilled and the trocar/drill has been removed, and further illustrates a flexible guide wire member threaded through the transverse tunnel and the femoral tunnel; a partial cut-away view of the upper end of a looped ligament graft is shown emplaced in the femoral tunnel.
Figure 5:
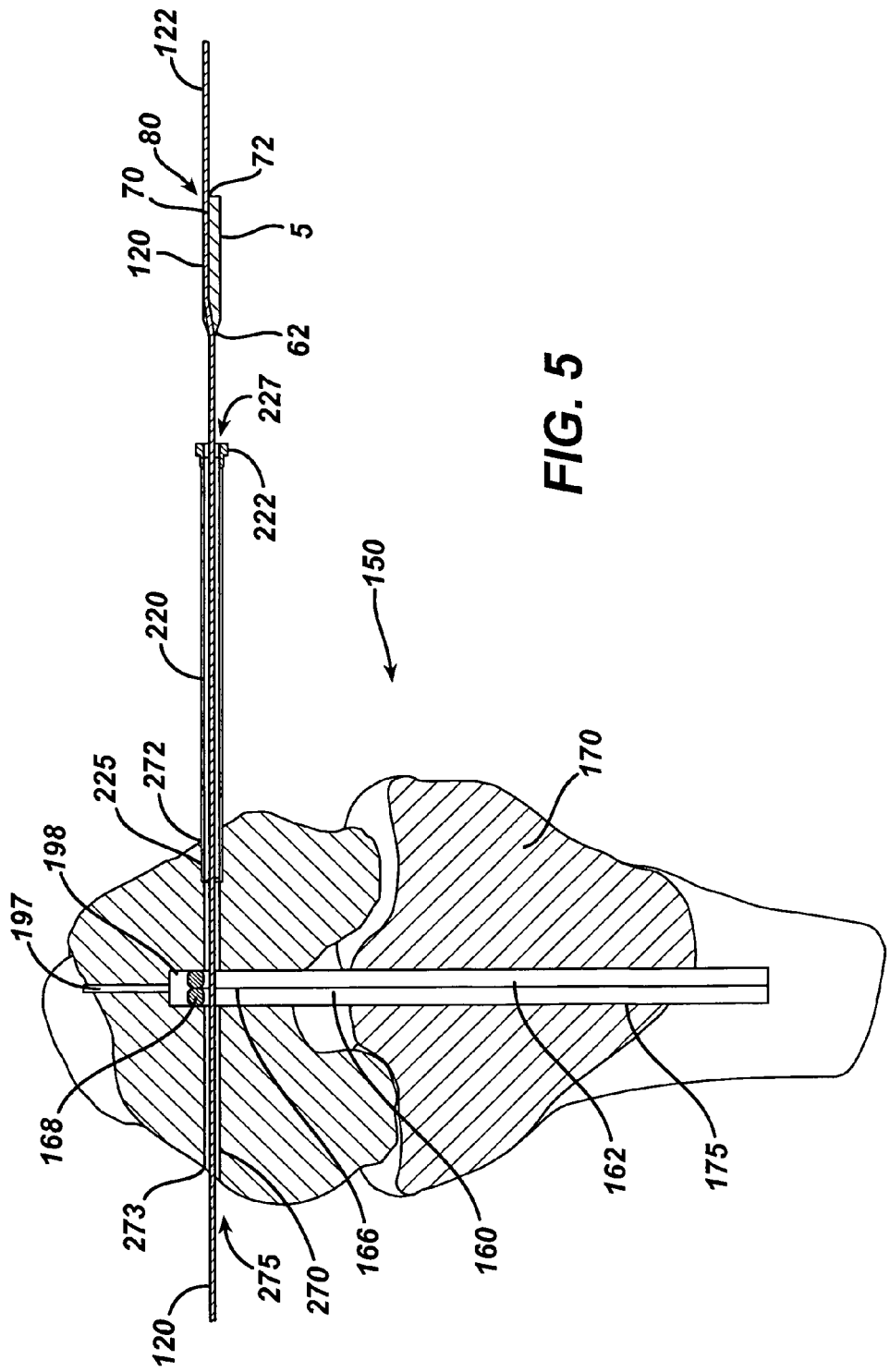
FIG. 5 illustrates a cross-pin of the present invention threaded onto the guide wire extending through a transverse tunnel in a femur.
Figure 6:
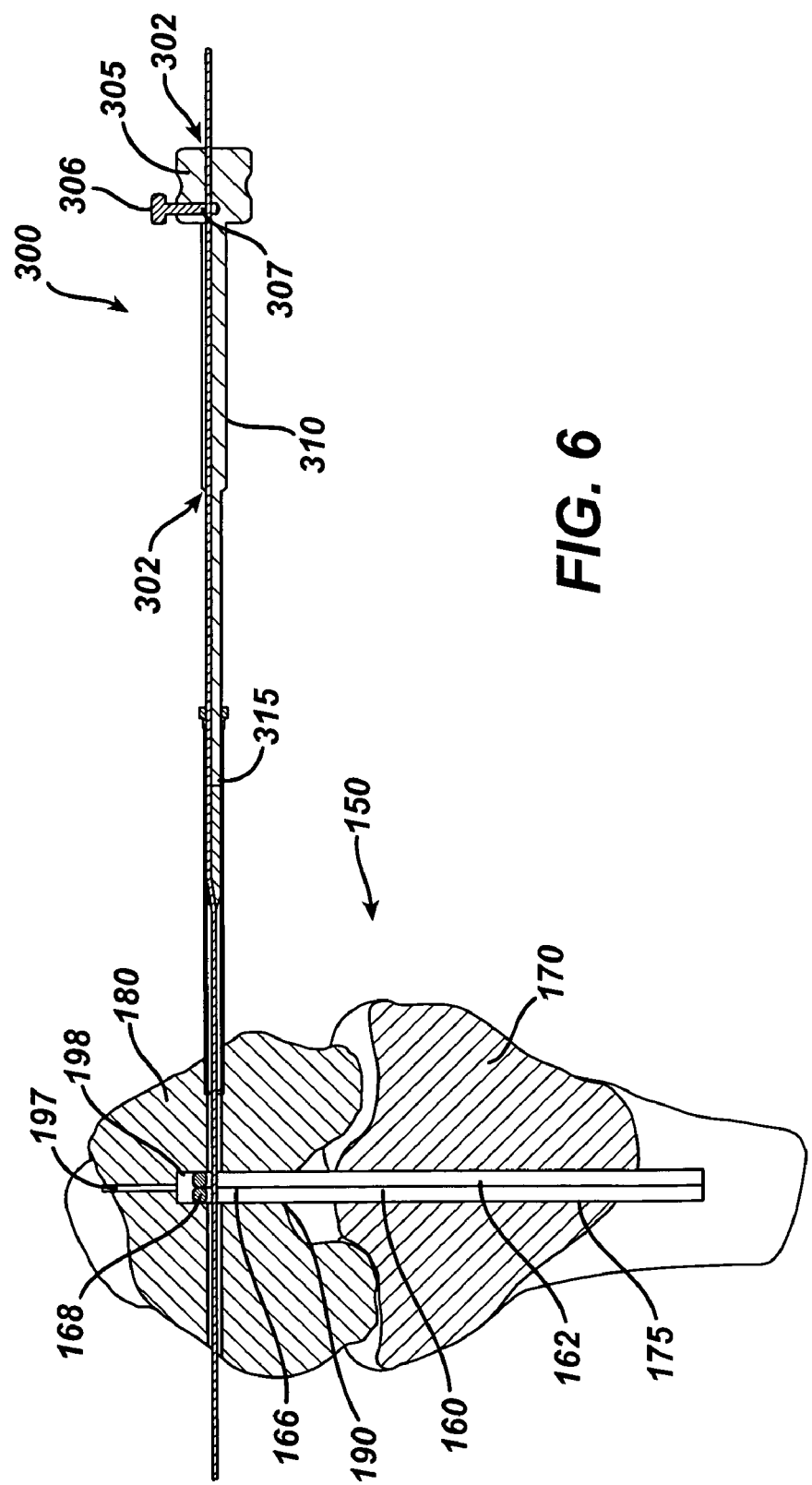
FIG. 6 illustrates an insertion rod threaded onto the guide wire and in contact with the proximal end of the cross-pin immediately prior to emplacement in the transverse tunnel.
Figure 7:
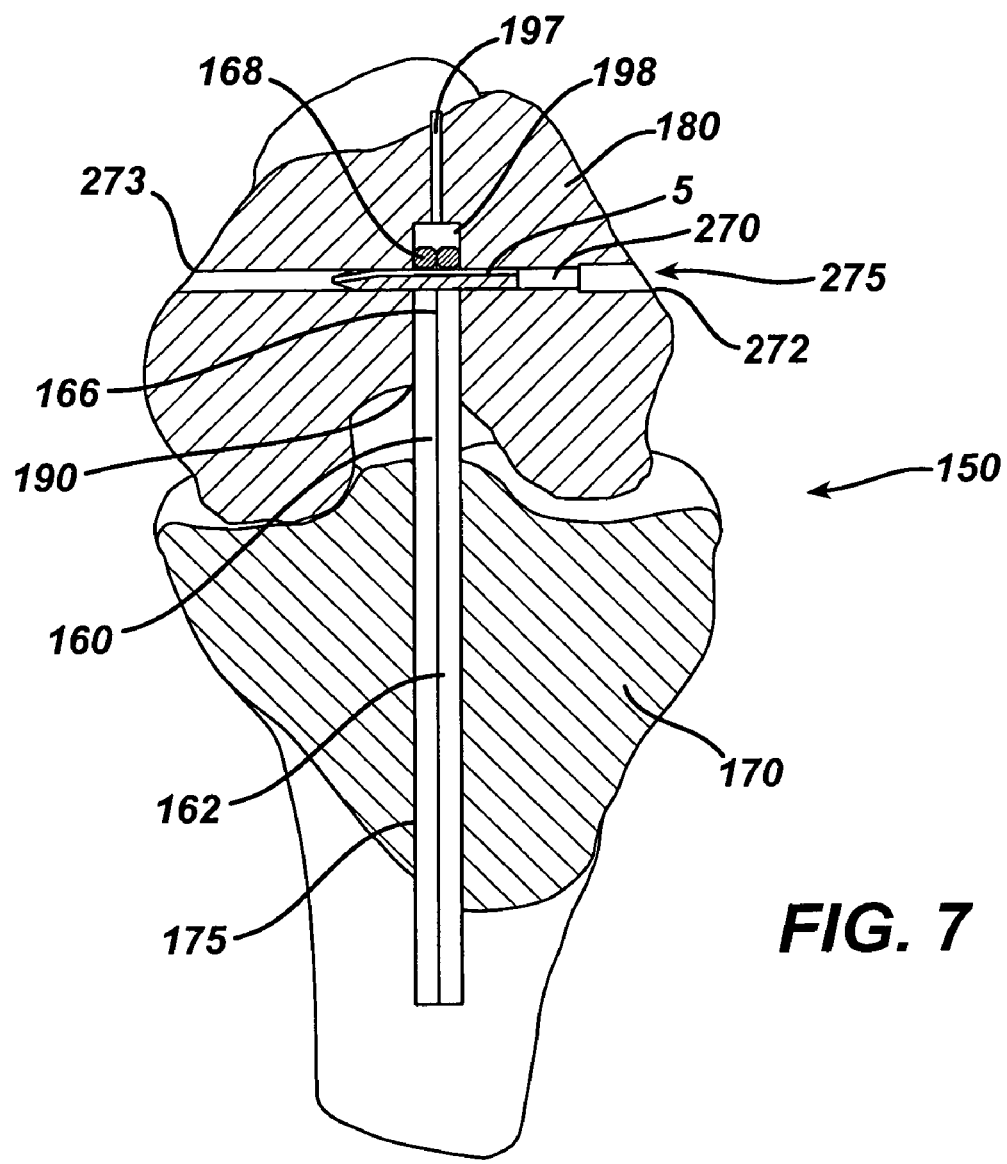
FIG. 7 illustrates the cross-pin of the present invention threaded over a guide wire and implanted in the transverse tunnel such that the cross-pin is beneath the top of an ACL graft; fixation of the lower end of the graft in the tibial tunnel is not illustrated.

A method of using the novel cross-pins of the present invention to secure the end of a graft in a bone tunnel is now described. Referring to now to FIGS. 3-7, the novel cross-pin 5 of the present invention is seen used to secure an ACL graft 200 in a femoral bone tunnel 190 contained in a femur 180 of a knee 150. Typically in such a procedure, a patient is prepared by the orthopedic surgeon in a conventional manner by immobilizing the patient's knee 150 in a desired configuration. Then, in a conventional manner longitudinal or axial bone tunnels are drilled in the ends of the tibia 170 and the femur 180 adjacent to patient's knee 150 (See FIG. 3). The tibial tunnel 175 and the femoral tunnel 190 are seen to be in substantial alignment. In addition, a transverse tunnel 270 is drilled into the femur 190 such that the traverse tunnel 270 intersects the femoral tunnel 190 toward the top 198 of the femoral tunnel 190. This can be done in a variety of conventional manners. For example as seen in FIG. 3, a conventional trocar drill member 210 is affixed with a pin 211 in a conventional cannula sleeve 220. The trocar drill member 210 has pointed distal end 212 and flat proximal end 215. Cannula sleeve 220 has proximal end 222, distal end 225 and passage way 227. The proximal end 215 is mounted to a conventional surgical drill and the distal end 212 drills through the femur 180 to create the transverse tunnel 270, while emplacing at least a portion of the distal end 225 of cannula sleeve 220 therein. Other conventional methods of drilling the transverse tunnel and emplacing the cannula sleeve 220 may be used as well. Transverse tunnel 270 has opposed open ends 272 and 273, and passage 275. After the trocar or drill has been removed from tunnel 270, an ACL replacement graft 160 is moved into the femoral tunnel 190 in a conventional manner, for example, by attaching to sutures that are pulled through suture tunnel extension 197. A conventional guide wire 120 is threaded through the transverse tunnel 270 through such that a portion of the guide wire 120 is beneath the top 168 of the upper end 166 of the looped ACL graft 160. Conventional techniques and equivalents thereof may be used to thread the guide wire 120 and move the graft 160 into place. Guide wires used in this art are conventionally known and may be made of a variety of biocompatible materials including surgical stainless steel, Nylon, Nitinol, etc. Initially, the cross-pin 5 is threaded onto a guide wire 120 by inserting a first end 122 of the guide wire 120 into the guide wire opening 62 in nose member 55 and threading the guide wire 120 through the tunnel 100 out of passage 102 and into passage 80 of the trough 70. The end 122 of the guide wire 120 exits the proximal end 72 of the trough 70 through an opening 22 in the proximal end 20 of the cross-pin 5. The guide wire 120 is then threaded through the insertion instrument 300. The instrument 300 is seen to have a proximal handle 305 and an elongated member 310 having a distal end 315. The insertion instrument 300 has a lumen or longitudinal passage 302 running the length of the instrument. The instrument 300 is seen to have set screw 306 having distal end 307 that is moveable into passage 302 in handle 305 to optionally engage guide wire 120. The distal end 315 of instrument 300 is located to engage the proximal end 20 of cross-pin 5. Then, the cross-pin 5 of the present is moved by the insertion tool 300 (via pushing, hammering, etc.) through the cannula sleeve and into tunnel 270 such that it is positioned in the femoral tunnel 190 underneath the top 166 of ACL graft 160 in the transverse tunnel 270 and upper femoral tunnel 198. Optionally, the insertion instrument is maintained in a fixed position relative to the guide wire 120 by the set screw 306, although it may also be slid along the wire 120. This implantation of the cross-pin 5 secures the end 166 of the ACL graft 160 in the femoral tunnel 190. The guide wire 120 is then removed along with the cannula sleeve 220 and this portion of the surgical procedure is completed. The other end 162 of ACL graft is secured in the tibial tunnel 175 using conventional securing procedures and techniques such as the use of interference screws or cross-pins (not shown). This then completes the surgical procedure and the reconstruction of the knee 150 with the ACL graft 160 secured in place. Although not shown, a knot may be placed in the guide wire 120 distal to the nose member 50. The knot will have an overall dimension larger than the maximum dimension of the guide wire opening 62. Then, if the surgeon desires to remove the cross-pin 5 after emplacement in transverse tunnel 270 for any reason during any stage of the procedure, the surgeon pulls proximally on the guidewire 120 to back-out and remove the cross-pin 5.

The novel method and cross-pin 5 of the present invention have many advantages. The advantages include the ability to remove pin at time of surgery, and, no uni-cortical fixation (equal distribution of load across the device). In addition the pin is centered in the femoral tunnel and a single size implant may be used.

Although this invention has been shown and described with respect to detailed embodiments thereof, it will be understood by those skilled in the art that various changes in form and detail thereof may be made without departing from the spirit and scope of the claimed invention.

We claim:

1. An implantable cross-pin for use in an ACL repair procedure, comprising:
   an elongated member having a proximal end, a distal end, a central longitudinal axis extending between the proximal and distal ends, and an outer surface;
   a nose member extending out from the distal end of said elongated member having a proximal end and a distal end;
   an axial trough in the elongated member extending though the outer surface, said trough having a proximal end, a distal end, a bottom, opposed ends, an open top, and a passageway, the passageway aligned with the central longitudinal axis;
   a guide wire opening in the distal end of the nose member and concentric with the central longitudinal axis of the elongated member;
   an interior tunnel having a passage with an enclosed circular perimeter in the nose member extending from the guide wire opening and extending into the trough such that the passage is in communication with the guide wire opening and the trough, the interior tunnel being obliquely oriented relative to the central longitudinal axis of the elongated member; and
   a guide wire seated in the axial trough and extending through the interior tunnel and the guide wire opening;
   wherein the cross-pin comprises a biocompatible material.

2. The cross-pin of claim 1, wherein the material is bioabsorbable.

3. The cross-pin of claim 2, wherein the bioabsorbable material is selected from the group consisting of PLA, PGA, and copolymers thereof.

4. The cross-pin of claim 1, wherein the proximal end of the cross-pin comprises an opening in communication with the proximal end of the trough.

5. The cross-pin of claim 1, wherein the nose member has a bullet shape.

* * * * *